US011123490B2

(12) United States Patent
Pommereau et al.

(10) Patent No.: US 11,123,490 B2
(45) Date of Patent: Sep. 21, 2021

(54) DRUG DELIVERY DEVICE WITH TAMPER-EVIDENT CLOSURE

(71) Applicant: SANOFI-AVENTIS DEUTSCHLAND GMBH, Frankfurt am Main (DE)

(72) Inventors: Christian Pommereau, Frankfurt am Main (DE); Gunther Sendatzki, Frankfurt am Main (DE); Stefan Kamlot, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 0 days.

(21) Appl. No.: 15/840,357

(22) Filed: Dec. 13, 2017

(65) Prior Publication Data
US 2018/0099097 A1 Apr. 12, 2018

Related U.S. Application Data

(63) Continuation of application No. 14/414,742, filed as application No. PCT/EP2013/066557 on Aug. 7, 2013, now abandoned.

(30) Foreign Application Priority Data
Aug. 8, 2012 (EP) .................................. 12179603

(51) Int. Cl.
A61M 5/24 (2006.01)
A61M 5/50 (2006.01)

(52) U.S. Cl.
CPC ........ A61M 5/2455 (2013.01); A61M 5/5086 (2013.01)

(58) Field of Classification Search
CPC .... A61M 5/50; A61M 5/5086; A61M 5/2455; A61M 5/285; A61M 5/3202; A61M 2005/3104; A61M 2005/3106; A61M 2005/311; A61M 2005/312; A61M 39/0613; A61M 39/14; A61M 2039/0294; A61M 2039/042; A61M 5/2033;
(Continued)

(56) References Cited

U.S. PATENT DOCUMENTS 533,575 A 2/1895 Wilkens
4,666,063 A 5/1987 Holoubek et al.
(Continued)

FOREIGN PATENT DOCUMENTS

CA 2138528 C 12/1998
CA 2359375 A1 7/2000
(Continued)

OTHER PUBLICATIONS

International Search Report for Int. App. No. PCT/EP2013/066557, completed Sep. 24, 2013.
(Continued)

Primary Examiner — Bhisma Mehta
Assistant Examiner — James D Ponton
(74) Attorney, Agent, or Firm — Fish & Richardson P.C.

(57) ABSTRACT

The present invention relates to a drug delivery device for dispensing of a dose of a medicament, comprising a housing to accommodate a cartridge being at least partially filled with a medicament, wherein the housing comprises a dispensing end with an access opening which is closed by a tamper-evident closure.

22 Claims, 3 Drawing Sheets

(58) Field of Classification Search
CPC ........ A61M 5/2407; A61M 2005/2407; B65D 2251/0015; B65D 2251/0071; B65D 51/228

See application file for complete search history.

(56) References Cited

U.S. PATENT DOCUMENTS

| | | | |
|---|---|---|---|
| 4,688,703 | A | 8/1987 | Bayer |
| 4,865,591 | A | 9/1989 | Sams |
| 5,092,842 | A | 3/1992 | Bechtold et al. |
| 5,161,681 | A | 11/1992 | Kemp et al. |
| 5,226,895 | A | 7/1993 | Harris |
| 5,226,896 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,378,233 | A | 1/1995 | Haber et al. |
| 5,383,865 | A | 1/1995 | Michel |
| 5,391,157 | A | 2/1995 | Harris et al. |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A * | 11/1997 | Chanoch .............. A61M 5/3146 222/309 |
| 5,807,346 | A | 9/1998 | Frezza |
| 5,820,602 | A | 10/1998 | Kovelman et al. |
| 5,851,079 | A | 12/1998 | Horstman et al. |
| 5,921,966 | A | 7/1999 | Bendek et al. |
| 5,957,896 | A | 9/1999 | Bendek et al. |
| 5,961,495 | A | 10/1999 | Walters et al. |
| 6,004,297 | A | 12/1999 | Steenfeldt-Jensen et al. |
| 6,193,688 | B1 | 2/2001 | Balestracci et al. |
| 6,193,698 | B1 | 2/2001 | Kirchhofer et al. |
| 6,196,998 | B1 | 3/2001 | Jansen et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,562,006 | B1 | 5/2003 | Hjertman et al. |
| 6,613,023 | B2 | 9/2003 | Kirchhofer et al. |
| 6,699,224 | B2 | 3/2004 | Kirchhofer et al. |
| 6,899,698 | B2 | 5/2005 | Sams |
| 6,932,794 | B2 | 8/2005 | Giambattista et al. |
| 6,936,032 | B1 | 8/2005 | Bush, Jr. et al. |
| 7,169,132 | B2 | 1/2007 | Bendek et al. |
| 7,241,278 | B2 | 7/2007 | Moller |
| 7,614,514 | B2 | 11/2009 | Fuchs |
| 7,678,084 | B2 | 3/2010 | Judson et al. |
| 7,839,288 | B2 * | 11/2010 | Wang ............... G06K 19/07798 340/572.8 |
| 7,850,662 | B2 | 12/2010 | Veasey et al. |
| 7,973,664 | B1 * | 7/2011 | Lambert .......... G06K 19/07771 340/572.8 |
| 8,187,233 | B2 | 5/2012 | Harms et al. |
| 8,695,819 | B1 * | 4/2014 | Anderson .......... B65D 51/2835 215/6 |
| 2002/0052578 | A1 | 5/2002 | Moller |
| 2002/0120235 | A1 | 8/2002 | Enggaard |
| 2002/0188259 | A1 | 12/2002 | Hickle et al. |
| 2003/0050609 | A1 | 3/2003 | Sams |
| 2004/0059299 | A1 | 3/2004 | Moller |
| 2004/0097883 | A1 | 5/2004 | Roe |
| 2004/0210199 | A1 | 10/2004 | Atterbury et al. |
| 2004/0225258 | A1 | 11/2004 | Balestracci |
| 2004/0267207 | A1 | 12/2004 | Veasey et al. |
| 2005/0113765 | A1 | 5/2005 | Veasey et al. |
| 2005/0162277 | A1 * | 7/2005 | Teplitxky ............... B65D 55/06 340/572.8 |
| 2006/0153693 | A1 | 7/2006 | Fiechter et al. |
| 2006/0206057 | A1 | 9/2006 | DeRuntz et al. |
| 2007/0016143 | A1 | 1/2007 | Miller et al. |
| 2007/0088288 | A1 | 4/2007 | Barron et al. |
| 2008/0097310 | A1 * | 4/2008 | Buehler ................ A61M 5/50 604/111 |
| 2009/0275916 | A1 | 11/2009 | Harms et al. |
| 2010/0094214 | A1 * | 4/2010 | Abry .................. A61M 5/2033 604/110 |
| 2011/0015578 | A1 | 1/2011 | Lowke |
| 2011/0046550 | A1 | 2/2011 | Schiller et al. |
| 2012/0136334 | A1 * | 5/2012 | De Sausmarez Lintell ................ A61M 5/2448 604/500 |
| 2013/0096511 | A1 * | 4/2013 | MacArthur ......... A61M 5/3129 604/189 |
| 2013/0245561 | A1 * | 9/2013 | Kouyoumjian ......... A61M 5/20 604/191 |
| 2013/0281962 | A1 * | 10/2013 | James .................... A61M 5/24 604/404 |
| 2014/0008366 | A1 * | 1/2014 | Genosar .............. A61M 5/2448 220/265 |

FOREIGN PATENT DOCUMENTS

| | | |
|---|---|---|
| EP | 0496141 A1 | 7/1992 |
| EP | 0897729 A2 | 2/1999 |
| EP | 0937471 | 8/1999 |
| EP | 3937476 | 8/1999 |
| EP | 1776975 A2 | 4/2007 |
| JP | 2008-502422 | 1/2008 |
| JP | 2009-534080 | 9/2009 |
| WO | 93/07922 | 4/1993 |
| WO | 93/24160 A1 | 12/1993 |
| WO | 99/38554 | 8/1999 |
| WO | 01/10484 | 2/2001 |
| WO | 02/30495 | 4/2002 |
| WO | 02/055140 | 7/2002 |
| WO | 02/092153 A2 | 11/2002 |
| WO | 03/080160 A1 | 10/2003 |
| WO | 2006/084876 | 8/2006 |
| WO | WO 2007/122473 | 11/2007 |
| WO | 2011/127279 | 10/2011 |
| WO | 2011/131779 A1 | 10/2011 |
| WO | 2012/017063 A2 | 2/2012 |
| WO | 2012/020083 A1 | 2/2012 |
| WO | 2012/076626 | 6/2012 |
| WO | 2012/089620 A2 | 7/2012 |

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.

International Preliminary Report on Patentability in International Application No. PCT/EP2013/066557, dated Feb. 10, 2015, 5 pages.

"British Standard Specification for Spring Washers for General Engineering and Automobile Purposes—Metric Series," British Standards Institution, BS 4464, May 19, 1969, 14 pages.

* cited by examiner

DRUG DELIVERY DEVICE WITH TAMPER-EVIDENT CLOSURE

CROSS REFERENCE TO RELATED APPLICATIONS

The present application is a continuation of U.S. patent application Ser. No. 14/414,742, filed Jan. 14, 2015, which is a U.S. National Phase Application pursuant to 35 U.S.C. § 371 of International Application No. PCT/EP2013/066557 filed Aug. 7, 2013, which claims priority to European Patent Application No. 12179603.1 filed Aug. 8, 2012. The entire disclosure contents of these applications are herewith incorporated by reference into the present application.

TECHNICAL FIELD

The present invention relates to a drug delivery device, in particular to an injection device, such like a pen-type injector having a tamper-evident closure to provide a tamper-evident seal for protecting the interior of the device prior to a first use.

BACKGROUND

Drug delivery devices allowing for multiple dosing of a required dosage of a liquid medicament, such as liquid drugs, and further providing administration of the medicament to a patient, are as such well-known in the art. Generally, such devices have substantially the same purpose as that of an ordinary syringe. They may be designed as an injection device, e.g. as a pen-type injector.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge that has a moveable piston or bung mechanically interacting with a piston rod of a drive mechanism of the drug delivery device. By applying thrust to the piston in a distal direction, a predefined amount of the medicament can be expelled from the cartridge.

Drug delivery devices of e.g. pen-injector type typically comprise a distal housing component that serves as a cartridge holder and further comprise a proximal housing component to engage with the distal housing component and being further adapted to accommodate a drive mechanism to operably engage with the cartridge for dispensing a predefined amount of the medicament provided therein.

With drug delivery devices, such like pen-type injectors of disposable or reusable type a needle assembly comprising a needle hub and a double-tipped injection needle is to be removably arranged on a distal dispensing end of the housing of the drug delivery device. Typically, the distal end of the device may serve as a cartridge holder comprising an access opening to receive a proximally extending portion of the needle. The cartridge located in the distal housing portion or cartridge holder typically comprises a piercable seal, such like a septum being penetrable by the injection needle.

Especially with disposable drug delivery devices, wherein the cartridge filled with the medicament is readily disposed and assembled in the housing of the device, counterfeiters or falsifiers may access the cartridge via the dispensing end and may withdraw at least part of the medicament located therein. Since such unauthorized withdrawal of the medicament is not perceivable or detectable by the end user, there may arise a danger of health, when the product contained in the cartridge has been manipulated even prior to a first use of the device.

It is therefore an object of the present invention to improve patient safety and to inhibit unauthorized withdrawal of a medicament from a cartridge being readily assembled in a drug delivery device. A respective anti-counterfeiting means should be cost-efficient and easy to realize. Furthermore, the device should be easy and intuitive in handling by the end user or patient.

SUMMARY

In a first aspect the invention relates to a drug delivery device for dispensing of a dose of a medicament. In particular, the drug delivery device is an injection device, such like a pen-type injector for administering a dose of the medicament by way of injection. The drug delivery device comprises a housing to accommodate a cartridge being at least partially filled with the medicament to be dispensed. The housing, which accommodates the cartridge comprises a dispensing end, preferably at a distal end section thereof, which faces towards the patient. The dispensing end has an access opening which is closed by a tamper-evident or tamper-proof closure.

Prior to a first use and prior to a first insertion of an injection needle into or through the access opening the tamper-evident closure has to be removed or at least appropriately configured by the end user. A broken tamper-evident closure is therefore indicative that the drug delivery device has been manipulated. The end user or patient should be appropriately instructed to make use of the device only when the device comprises an undamaged and non-manipulated tamper-evident closure.

The initially present tamper-evident closure at least inhibits to insert a withdrawal device through the access opening of the dispensing end. Here, it may be sufficient when the tamper-evident closure simply blocks the access opening, thereby effectively hindering a withdrawal device, such like a cannula, to reach through the access opening.

The tamper-evident closure may therefore provide an effective anti-counterfeiting means, inherently indicating when a distal or dispensing end of the drug delivery device has been manipulated.

In a preferred embodiment the tamper-evident closure is removably disposed at the dispensing end of the housing. Preferably, the tamper-evident closure is assembled to or connected with the housing by means of a predetermined breaking structure or by means of a structurally weakened structure. The predetermined breakable connection of tamper-evident closure and housing serves to provide a well-defined and deliberate removal of the tamper-evident closure from the housing.

Instead of a complete separation and removal of the tamper-evident closure from the housing it is also conceivable that the tamper-evident closure is moved or pivoted in a predefined way relative to the housing in order to give way to the access opening. Hence, it is conceivable, that the tamper-evident closure is only partially connected with the housing via a predetermined breaking or scoring structure. Upon breaking of the predetermined breaking structure at least a pivoting of the tamper-evident closure relative to the housing may be enabled.

According to another embodiment, the tamper-evident closure protrudes from the dispensing end of the housing. Typically, the housing comprises a cylindrical or elongated shape, wherein the dispensing end is located at a longitudinal or axial end thereof. Preferably, the tamper-evident closure is designed as a longitudinal protrusion of the housing. Such a protruding tamper-evident structure may be easily gripped, bended, twisted or tilted with respect to the housing in order to give way to the access opening.

Moreover and according to another embodiment, the tamper-evident closure is integrally formed with the housing. Preferably, the housing and the tamper-evident closure may comprise or may be composed of an injection mouldable plastic material. This way, tamper-evident closure and housing of the drug delivery device can be manufactured and assembled in a single manufacturing step, e.g. by way of injection molding.

The colour of the tamper-evident closure might be different to the colour of the housing of the drug delivery device to improve a visual appearance and to implement a warning function of the tamper-evident closure. The colour of the closure may for instance be applied by means of printing, such like pad-printing or tampoprinting, offset-printing or the like or by means of a two- or more-component molding process or any other appropriate or comparable processes.

Typically, the housing and/or the tamper-evident closure may comprise a thermoplastic material, a technical polymer and/or a duroplastic polymer. Among thermoplastic materials, the housing may comprise polyolefins such like polyethylene (PE) or polypropylene (PP). Furthermore, polycarbonate (PC) and/or acrylonitrile butadiene styrene (ABS) may for instance be used as technical polymers. Generally, the material of the tamper-evident closure may be different from the material of the housing in order to improve breakability or hardness.

According to another preferred embodiment, the tamper-evident closure comprises an identification member, embedded in the bulk of the closure or being attached to an outer surface thereof. This way, a hybrid closure can be provided, wherein the identification member may for instance comprise a molded RFID chip inside or wherein the identification member may comprise a hologram, a datamatrix- and/or a QR code, e.g. provided on an outside facing surface of the closure. The identification member may enable the user to identify and to confirm the genuine origin of the said drug delivery device, e.g. by making use of electronic reading devices, such like smartphones or RFID-readers. Additionally, the identification member may also serve to store and to provide useful information to the user such as e.g. an expiry date, information for use of the medicament and/or of the device, the legal manufacturer and/or a time of a first attempt to break the closure.

In a further embodiment the dispensing end of the housing and the tamper-evident closure are mutually and firmly bonded or adhesively interconnected. For instance, the tamper-evident closure may be provided as a separate component bonded or adhesively connected with the dispensing end of the housing. For instance, it may be attached to the housing by means of a peelable foil. This way, also existing delivery devices and respective housing designs could be retrofitted with a tamper-evident closure.

In any case, the mutual interconnection of tamper-evident closure and dispensing end of the housing is of non-resurrecting type. Once the interconnection is abrogated it cannot be re-established. Preferably, tamper-evident closure and dispensing end of the housing are frangibly interconnected.

In a further preferred embodiment, the tamper-evident closure entirely seals the access opening of the housing. Hence, by way of the tamper-evident closure, a distal or dispensing end of the housing can be hermetically sealed. This way the interior of the device can be protected against environmental influence. Ingress of dirt, dust or humidity into the interior of the housing can be therefore effectively prevented.

In a further embodiment, an outer circumference of the tamper-evident closure is larger than the cross section of the access opening. Typically, the tamper-evident closure comprises a disc-like shape, wherein only a radial central portion of the disc is integrally formed or connected with the housing of the drug delivery device. A circumferential, radially outwardly extending portion of the tamper-evident closure may serve as an effective gripping means for effectively inducing a tilting and/or twisting motion of the tamper-evident closure relative to the housing. By increasing the cross section or radial extension of the tamper-evident closure, a force-effect provided by a user can be effectively enhanced due to a kind of a leverage effect.

As a consequence, the radial cross section of a disc-shaped portion of the tamper-evident closure is larger than a stepped down neck portion thereof by way of which the tamper-evident closure is interconnected with the dispensing end of the housing.

In a further embodiment, the outer circumference of the tamper-evident closure comprises a serrated, corrugated or keyed structure. This way, improved grip and a friction-reduced handling of the tamper-evident closure can be provided. Furthermore, correspondingly shaped tools may be used in order to induce a motion, a twisting or tilting of the tamper-evident closure for releasing and/or removing the same from the housing. Especially for an improved counterfeit protection, the use of a specific and appropriate geometry, e.g. of a Torx- or star key-profile of the radial extension of the closure together with a corresponding profile of a means or of a tool to remove the closure, might become necessary.

According to another embodiment, the access opening of the housing is located in a distal end face of a threaded socket of a cartridge holder which is adapted to receive a double-tipped needle assembly. The cartridge holder typically forms a distal or dispensing end of the drug delivery device. Typically, the housing further comprises a body as a proximal housing component which serves to receive or which comprises a drive mechanism, typically having a piston rod to operably engage with a piston of the cartridge. The drive mechanism may further comprise a dose dial and a dose button by way of which the size of a dose to be dispensed can be individually set and subsequently dispensed.

During a dispensing action, the piston rod of the drive mechanism is urged in distal direction, thereby driving the piston of the cartridge towards the distal dispensing end of the cartridge and the housing of the drug delivery device. Distally directed displacement of the piston of the cartridge leads to a respective expelling of the medicament from the cartridge when a double-tipped needle is in fluid communication with the interior volume of said cartridge. The double tipped needle assembly typically comprises a needle hub having a threaded receptacle to be releasably mounted on the threaded socket of the cartridge holder.

Upon screwing the needle assembly onto the threaded socket, a proximally extending tipped needle end pierces and penetrates a distally located seal of the cartridge located inside and fixed by the cartridge holder.

In a further preferred embodiment, the drug delivery device comprises a removable protective cap to releasably cover the dispensing end of the housing of the drug delivery device. Typically, the protective cap serves to cover the complete cartridge holder of the drug delivery device. The protective cap comprises a cupped receptacle to receive the dispensing end of the housing even with the tamper-evident closure assembled thereon. By means of the protective cap, the cartridge holder as well as the dispensing end of the housing of the drug delivery device can be effectively protected again environmental influences, such like dirt, dust and/or humidity.

According to another embodiment, the cap comprises a receptacle at an outside facing portion to receive and/or to engage with the tamper-evident closure. This way, the cap may serve as a tool to grip and to induce a breaking motion onto the tamper-evident seal for removing the same prior to an initial use of the drug delivery device.

It is of particular benefit here, when the receptacle and the tamper evident closure positively engage when the tamper-evident closure is received in the receptacle of the protective cap. This way the cap may effectively provide a tool for removing and/or releasing the tamper-evident closure from the housing.

In a further preferred embodiment, the receptacle to receive and/or to engage with the tamper-evident closure is located at a distal end portion of the protective cap. Removal of the tamper-evident closure then requires to initially remove the protective cap from the drug delivery device, to twist the protective cap by about 180° and to mount the receptacle of the protective cap onto the tamper-evident closure. Then, a releasing or breaking motion of the tamper-evident closure may be induced by means of the protective cap, which according to its geometric structure and a comparatively large diameter compared to the cross section of the tamper-evident closure, may provide a leverage effect.

Moreover, the geometric structure of the protective cap may allow for an easy and intuitive gripping of the cap itself for inducing a twisting motion to the tamper-evident closure relative to the housing or cartridge holder of the device.

According to another embodiment, the receptacle comprises a sidewall that mates and corresponds with the outer circumference of the tamper-evident closure. If the tamper-evident closure comprises a serrated, corrugated or keyed structure, the sidewall of the receptacle of the protective cap also comprises a correspondingly shaped serrated, corrugated or keyed structure. This way, a positive engagement comparable to a screw-driver interconnection can be provided allowing to induce a releasing and twisting motion onto the tamper-evident closure relative to the housing or cartridge holder.

According to further embodiment the tamper-evident closure and the receptacle comprise mutually corresponding geometric structures in order to mutually engage for transferring an angular momentum from the protective cap to the tamper-evident closure for releasing and/or removing the same from the dispensing end of the drug delivery device.

Other solutions may include tamper-evident closures that are to be released or to be removed from the dispensing end of the drug delivery device by way of tilting, by way of impressing or by indenting a structurally weakened portion of the interconnection of tamper-evident closure and dispensing end of the housing.

Furthermore and according to another embodiment, the drug delivery device comprises or is designed as an injection device such like a pen-type injector. Preferably, the drug delivery device is of disposable type device having a cartridge readily disposed therein. After use, when the cartridge is substantially emptied the entire device is then intended to be discarded instead of replacing the cartridge by a new one.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2, des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiment of the invention will be described by making reference to the drawings, in which.

DETAILED DESCRIPTION

Figure 1:
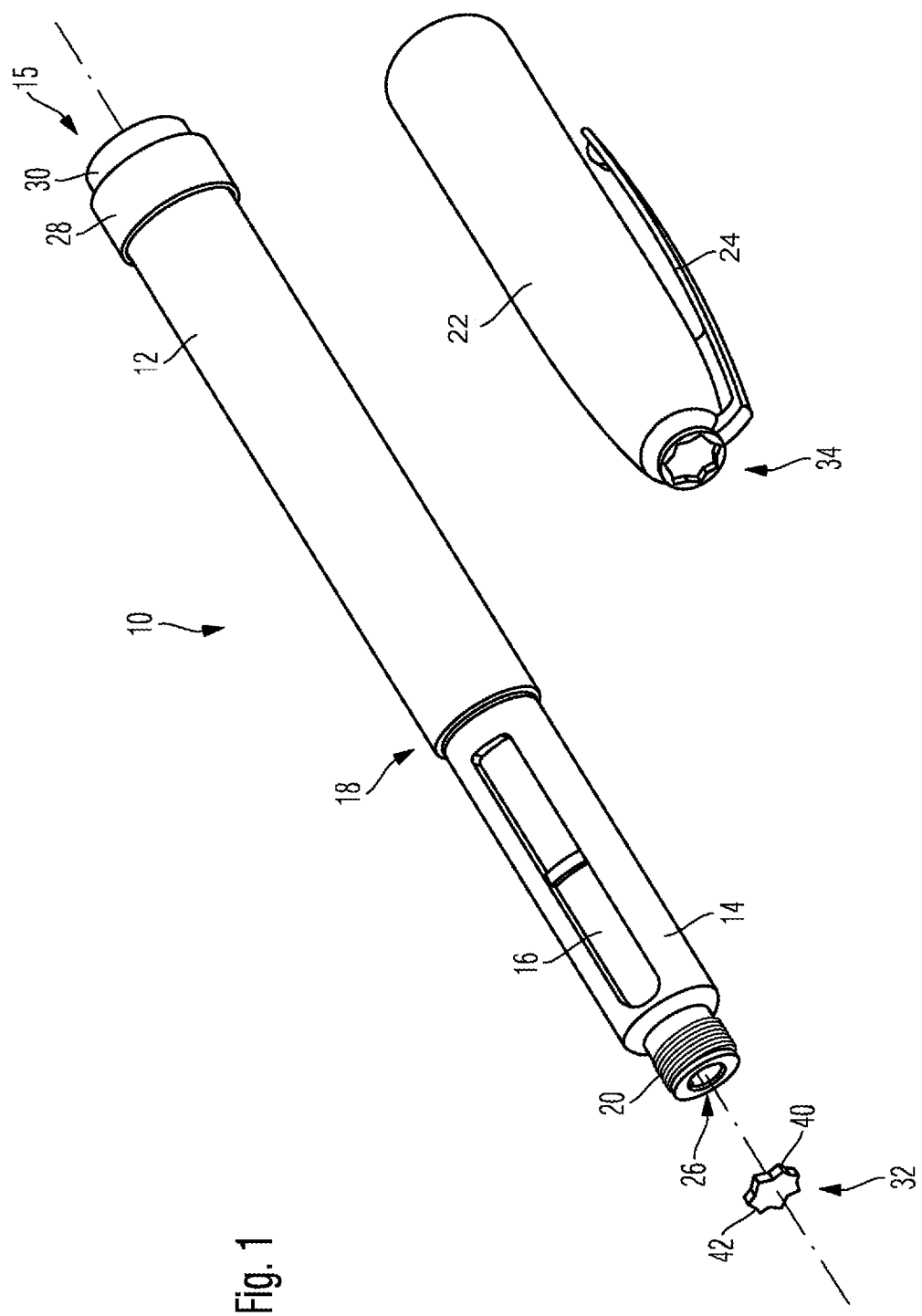
FIG. 1 schematically illustrates the various components of the drug delivery device in a perspective view after removal and/or separation of a tamper-evident closure, FIG. 2 schematically illustrates the dispensing or distal end of a cartridge holder with a tamper-evident closure and FIG. 3 schematically shows the distal end portion of a protective cap featuring a receptacle to mate with the geometric structure of the tamper-evident closure according to FIG. 2.

The drug delivery device 10 as illustrated in FIG. 1 comprises a housing having a proximal body 12 and a distally located cartridge holder 14. Body 12 and cartridge holder 14 are mutually interconnected in an interface section 18, in which cartridge holder 14 and body 12 are arranged in a mutually overlapping or interleaved configuration. There, body 12 and cartridge holder 14 may be inseparably or permanently interconnected, e.g. by way of welding or by means of an adhesive. Moreover, when designed as a reusable device, body 12 and cartridge holder 14 may be releasably engaged. For instance, body 12 and cartridge holder 14 may be threadedly engaged in the interface section 18.

Figure 2:
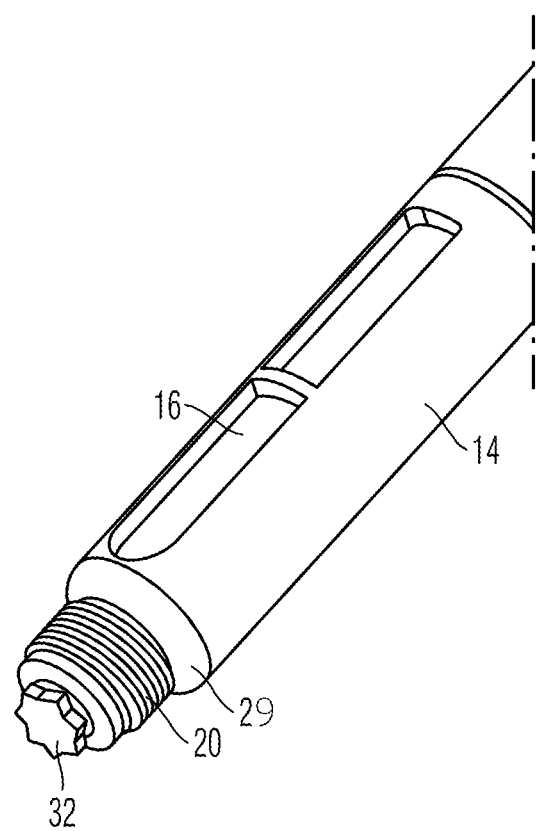

A proximal end of the drug delivery device is provided with a dose dial 28 and a proximal dose button 30. By way of turning or twisting the dose dial 28, a size of a dose of a medicament to be dispensed by the device 10 can be individually selected and set. Once, a dose has been appropriately set, by means of pushing the dose button 30 in distal direction, hence towards the cartridge holder 14, the drive mechanism housed in the body 12 may serve to axially displace a piston rod in distal direction for correspondingly urging a piston of a cartridge in distal direction for expelling a predefined amount of the medicament from the cartridge which is positioned in and fixed by the cartridge holder 14. As further illustrated in FIG. 2, the cartridge holder 14 comprises a shoulder portion 29 against which a correspondingly shaped cartridge may axially and/or radially abut when assembled therein.

As illustrated in FIG. 1 the cartridge holder 14 comprises an inspection window 16 by way of which a filling level of a vitreous cartridge mounted therein can be visually inspected.

At its distal end the cartridge holder 14 comprises a threaded and stepped-down socket 20 which is adapted to threadedly receive a double tipped needle assembly. The needle assembly, which is not particularly illustrated here, typically comprises a circular or cylindrically shaped hub having a threaded cylindrical portion to be screwed onto the threaded socket 20. Moreover, the needle assembly comprises a tipped needle end to enter the access opening 26 of the cartridge holder 14 for piercing and for penetrating a pierceable seal, e.g. a septum of the cartridge located in the cartridge holder 14.

Additionally, the drug delivery device 10 of pen-injector type comprises a protective cap 22 which is to be releasably arranged on the cartridge holder 14. The protective cap 22 comprises a clip 24 by way of which the drug delivery device 10 with the cap 22 mounted thereon can be clipped and fastened to e.g. a piece of cloth, like a pocket of a shirt. The protective cap 22 may positively engage with the interface section 18 and may further substantially flush with the outer circumference of the body 12 of the drug delivery device 10 when mounted on the cartridge holder 14.

Figure 3:
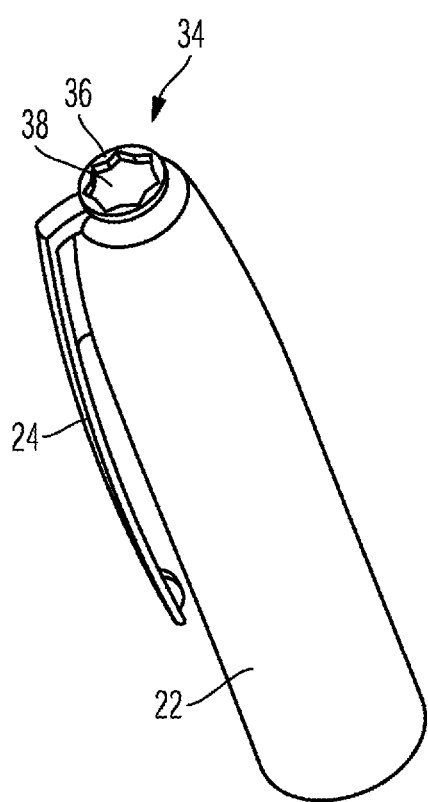

At its distal end, the protective cap 22 comprises a receptacle 34 having a substantially flat-shaped or flattened bottom portion 38 and a sidewall 36. The sidewall 36 as illustrated in FIGS. 1 and 3 comprises an inward facing serrated or corrugated surface that mates and corresponds with the geometry and outer circumference of a tamper-evident closure 32, which is separately illustrated in FIG. 1 and which is initially present at the distal end of the threaded socket 20 of the cartridge holder 14.

The tamper-evident closure 32 comprises a disc-like shape and features radially outwardly extending lobes 40 separated by radially inwardly extending grooves 42. The lobe-groove-structure of the outer circumference of the tamper-evident closure 32 strictly mates and corresponds with the radially inward facing geometry and structure of the protective cap 22. This way, when inserting the tamper-evident closure 32 in the receptacle 34, a positive engagement of protective cap 22 and tamper-evident closure can be provided by way of which an angular momentum between cap 22 and tamper-evident closure 32 can be transferred for releasing the tamper-evident closure 32 from the housing 12, 14.

Preferably, the tamper-evident closure 32 is integrally formed with the housing 14 of the drug delivery device 10. In particular, the tamper-evident closure 32 and the cartridge holder 14 may be manufactured by way of injection molding. This way, an initially sealed cartridge holder 14 can be easily provided without any further steps or efforts of assembly. Compared to existing designs of drug delivery devices, only a respective mold for the injection molding manufacturing of cartridge holder 14 and protective cap 22 has to be modified in order to provide a tamper-evident closure and a correspondingly shaped tool for irreversibly removing or abrogating an interconnection of the tamper-evident closure 32 and the cartridge holder 14.

The invention claimed is:

1. A drug injection device for dispensing of a dose of a liquid medicament, the drug injection device comprising:
    a housing to accommodate a container being at least partially filled with the liquid medicament, wherein the housing comprises a dispensing end with an access opening configured to receive a needle of a needle assembly in fluid communication with an interior of the container; and
    a tamper-evident closure closing the access opening, wherein the tamper-evident closure comprises an electronic identification member embedded inside the tamper-evident closure, wherein the electronic identification member in its entirety is arranged inside the tamper-evident closure, and wherein the electronic identification member is configured for wireless data transmission, and wherein an outer circumference of the tamper-evident closure comprises a serrated, corrugated, or keyed structure that protrudes radially outwardly.

2. The drug injection device according to claim 1, wherein the tamper-evident closure is removably disposed at the dispensing end of the housing.

3. The drug injection device according to claim 1, wherein the tamper-evident closure protrudes from the dispensing end of the housing.

4. The drug injection device according to claim 1, wherein the tamper-evident closure is integrally formed with the housing.

5. The drug injection device according to claim 1, wherein the tamper-evident closure seals the access opening of the dispensing end of the housing.

6. The drug injection device according to claim 1, wherein the outer circumference of the tamper-evident closure is larger than a diameter of the access opening.

7. The drug injection device according to claim 1, wherein the access opening is located in a distal end face of a threaded socket of a cartridge holder, and wherein the threaded socket is adapted to receive the needle assembly, the needle assembly comprising a double tipped needle.

8. The drug injection device according to claim 1, further comprising a protective cap comprising a receptacle at an outside facing portion to receive the tamper-evident closure.

9. The drug injection device according to claim 8, wherein the receptacle of the protective cap is adapted to positively engage with the outer circumference of the tamper-evident closure.

10. The drug injection device according to claim 9, wherein the receptacle is located at a distal end portion of the protective cap.

11. The drug injection device according to claim 9, wherein the receptacle comprises a sidewall that mates with the outer circumference of the tamper-evident closure.

12. The drug injection device according to claim 9, wherein the tamper-evident closure and the receptacle are adapted to mutually engage for transferring an angular momentum from the protective cap to the tamper-evident closure.

13. The drug injection device according to claim 1, wherein the drug injection device is designed as an injection device having the container disposed therein being at least partially filled with the liquid medicament.

14. The drug injection device according to claim 13, wherein the container comprises a cartridge sealed by a pierceable seal.

15. The drug injection device according to claim 1, wherein the electronic identification member comprises one of:
    a RFID Chip,
    a hologram,
    a datamatrix code, or
    a QR code.

16. The drug injection device according to claim 1, wherein the housing and the tamper-evident closure comprise an injection moldable plastic material.

17. The drug injection device according to claim 1, wherein the drug injection device is of a disposable type, the drug injection device comprising the container within the housing.

18. The drug injection device according to claim 17, wherein the housing comprises a body and a cartridge holder and wherein the body and the cartridge holder are inseparably or permanently interconnected.

19. A drug injection device for dispensing of a dose of a liquid medicament, the drug injection device comprising:
    a housing to accommodate a container being at least partially filled with the liquid medicament, wherein the housing comprises a dispensing end with an access opening configured to receive a needle of a needle assembly in fluid communication with an interior of the container; and
    a closure removably disposed at and directly connected to the dispensing end of the housing to close the access opening, wherein the closure comprises an electronic identification member embedded inside the closure, wherein the electronic identification member in its entirety is arranged inside the closure, wherein the electronic identification member is configured for wireless data transmission, and wherein an outer circumference of the closure comprises a serrated, corrugated, or keyed structure.

20. The drug injection device of claim 19, wherein the closure seals the access opening.

21. The drug injection device of claim 19, wherein the closure blocks the access opening to prevent the needle of the needle assembly from longitudinally traversing the access opening.

22. The drug injection device of claim 19, wherein the closure protrudes in a longitudinal direction from the dispensing end of the housing.

* * * * *